United States Patent
Chang et al.

(10) Patent No.: US 10,350,153 B2
(45) Date of Patent: Jul. 16, 2019

(54) TOPICAL COMPOSITIONS COMPRISING RETINOIDS AND LOW IRRITATION POLYMERIC CLEANSING AGENTS

(71) Applicant: Johnson & Johnson Consumer Inc., Skillman, NJ (US)

(72) Inventors: Michael Chang, Hoboken, NJ (US); Michael James Fevola, Belle Mead, NJ (US); Simarna Kaur, Neshanic Station, NJ (US); Michael D. Southall, Pennington, NJ (US); Ali Fassih, Flemington, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 6 days.

(21) Appl. No.: 15/475,565

(22) Filed: Mar. 31, 2017

(65) Prior Publication Data
US 2018/0280276 A1    Oct. 4, 2018

(51) Int. Cl.
| | |
|---|---|
| A61K 8/67 | (2006.01) |
| A61K 31/07 | (2006.01) |
| A61K 8/73 | (2006.01) |
| A61K 47/36 | (2006.01) |
| A61Q 19/08 | (2006.01) |
| A61K 9/00 | (2006.01) |
| A61K 9/113 | (2006.01) |
| A61K 8/06 | (2006.01) |
| A61Q 19/00 | (2006.01) |
| A61K 47/32 | (2006.01) |
| A61K 9/107 | (2006.01) |

(52) U.S. Cl.
CPC .............. *A61K 8/671* (2013.01); *A61K 8/732* (2013.01); *A61K 9/0014* (2013.01); *A61K 9/107* (2013.01); *A61K 9/113* (2013.01); *A61K 31/07* (2013.01); *A61K 47/32* (2013.01); *A61K 47/36* (2013.01); *A61Q 19/008* (2013.01); *A61Q 19/08* (2013.01); *A61K 8/062* (2013.01)

(58) Field of Classification Search
CPC ........ A61K 9/113; A61K 8/671; A61K 31/07; A61K 8/732; A61K 8/731; A61K 9/0014; A61K 47/36; A61K 47/32; A61K 9/10; A61K 9/06; A61K 8/062; A61Q 19/08; A61P 17/00
See application file for complete search history.

(56) References Cited

U.S. PATENT DOCUMENTS

| | | | |
|---|---|---|---|
| 2,661,349 A | 12/1953 | Caldwell et al. | |
| 5,776,476 A | 7/1998 | Billmers et al. | |
| 5,954,883 A | 9/1999 | Nagle et al. | |
| 6,433,061 B1 | 8/2002 | Marchant et al. | |
| 8,025,902 B2 | 9/2011 | Librizzi et al. | |
| 8,258,250 B2 | 9/2012 | Fevola et al. | |
| 2002/0110572 A1* | 8/2002 | Chandar ................ | A61K 8/062 424/401 |
| 2007/0166273 A1 | 7/2007 | Krivulka et al. | |
| 2009/0264527 A1 | 10/2009 | Roszell | |
| 2011/0081310 A1* | 4/2011 | Fevola ................... | A61K 8/732 424/78.17 |
| 2011/0251273 A1 | 10/2011 | Oddos et al. | |
| 2011/0281946 A1* | 11/2011 | Waddon ................ | A61K 8/671 514/552 |
| 2014/0265007 A1 | 9/2014 | Bruning et al. | |
| 2015/0359713 A1 | 12/2015 | Fassih et al. | |

FOREIGN PATENT DOCUMENTS

| | | |
|---|---|---|
| DE | 10224298 A | 12/2003 |
| EP | 2314274 A | 4/2011 |
| WO | WO 1996/37420 | 11/1996 |
| WO | WO 2002/065995 A | 8/2002 |
| WO | WO 2010/085753 | 7/2010 |

OTHER PUBLICATIONS

"Antiaging Action of Retinol: From Molecular to Clinical" by Bellemere et al., Skin Pharmacol. Physiol. 2009; 22:200-09. (Year: 2009).*
Neutrogena® Ultra Gentle Daily Cleanser, commercially available from Johnson & Johnson Consumer Inc., Sep. 2012.
Neutrogena® Rapid Wrinkle Repair, commercially available from Johnson & Johnson Consumer Inc., Apr. 2012.
Editor, "Can rosacea be cured with retinol?", Skin Products for Rosacea Treatment Recovery with the Best Rosacea Skin Products, Jan. 5, 2015; http://rosaceaskinproducts.com/can-rosacea-be-cured-with-retinol/ <retrieved from the internet Jan. 10, 2018>.
Eichenfield et al., "Topical retinoids: the cornerstone of acne therapy", *Dermatology Times* 29.8:S2(6), Aug. 2008.
Wikipedia "Tretinoin", last edited Nov. 22, 2017; https://en.wikipedia.org/wiki/Tretinoin <retrieve from the internet Jan. 10, 2018>.
European search report dated Jul. 31, 2018, for EP application 18165440.1.
Mintel, "5 Piece try-me skincare starter set", Dec. 2012 (XP002783214).
Mintel, "Acne treatment formulas", Sep. 2006 (XP002783215).
Mintel, "Neutrogena—Visibly Refined Facial Care Products—Pore refining facial wash", Sep. 2002 (XP002713424).
Mintel, "Sensitive skin system", Jun. 2009 (XP002783213).
Extended European search report and opinion dated Dec. 17, 2018, for EP application 18165440.1.

* cited by examiner

*Primary Examiner* — Theodore R. West

(57) ABSTRACT

Topical compositions comprising a retinoid, a low irritation polymeric cleansing agent and a cosmetically-acceptable topical carrier are provided. Such compositions provide improved retinoid activity for treating for example signs of skin aging, acne, or rosacea.

2 Claims, No Drawings

TOPICAL COMPOSITIONS COMPRISING RETINOIDS AND LOW IRRITATION POLYMERIC CLEANSING AGENTS

FIELD OF THE INVENTION

Topical compositions comprising a retinoid, a low irritation polymeric cleansing agent (LIPCA) and a cosmetically-acceptable topical carrier are provided. Such compositions provide improved retinoid activity for treating for example signs of skin aging, acne, or rosacea.

BACKGROUND OF THE INVENTION

Retinoids have been used in a variety of prescription and cosmetic topical compositions for treating skin conditions such as signs of skin aging, acne, and rosacea.

For example, tretinoin is used in prescription acne products as well as prescription anti-wrinkle products such as RENOVA® commercially available from Obagi Medical Products, Inc. Retinol is used in cosmetics such as NEUTROGENA® Rapid Wrinkle Repair® commercially available from Johnson & Johnson Consumer Inc. NEUTROGENA® Rapid Wrinkle Repair® is used to fade the look of wrinkles in skin, smooth fine lines, improve skin texture, and brighten skin tone. Retinol in particular has proven to be a highly efficacious and cost effective cosmetic ingredient, and improvements in its activity and delivery into the skin are always desirable.

U.S. Pat. No. 8,258,250 discloses superhydrophilic amphiphilic copolymers (SACs) and cleansing compositions containing them. SACs are a type of low irritation polymeric cleansing agent, and are especially mild and efficacious.

U.S. Pat. No. 8,025,902 discloses another class of low irritation polymeric cleansing agent, low molecular weight hydrophobically modified polymers (HMPs) and cleansing compositions containing them.

NEUTROGENA® Ultra Gentle Daily Cleanser commercially available from Johnson & Johnson Consumer Inc. contains potassium acrylates copolymer, an HMP.

WO 2010/085753 discloses a treatment regimen including cleansing at least a portion of an area of skin afflicted with rosacea with a cleanser; applying a composition comprising metronidazole to at least a portion of the afflicted area, and applying an anti-redness composition to at least a portion of the cleansed and metronidazole-treated area. Use of "gentle" skin cleansers CETAPHIL® (Galderma Laboratories) and NU-DERM® (Obagi Medical Products, Inc.) are disclosed. In addition, optional application of compositions comprising retinoids and other ingredients, are disclosed.

Applicants have now discovered that the activity of retinoids is surprisingly increased by combining them with LIPCAs. Accordingly, new topical compositions comprising a retinoid, a LIPCA, and a cosmetically-acceptable topical carrier are disclosed herein.

SUMMARY OF THE INVENTION

The invention provides a topical composition comprising a retinoid, a SAC and a cosmetically acceptable topical carrier.

The invention also provides a composition comprising about 0.001 to about 5 weight percent retinol and about 0.1 to about 5 weight percent sodium potato dextrin dodecenylsuccinate.

The invention further provides a method for treating skin, comprising topically applying to skin in need of treatment for signs of skin aging, acne, or rosacea a composition comprising a retinoid, a SAC and a cosmetically acceptable topical carrier.

The invention also provides a topical composition comprising a retinoid, an HMP and a cosmetically acceptable topical carrier.

The invention also provides a composition comprising about 0.001 to about 5 weight percent retinol and about 0.1 to about 5 weight percent potassium acrylates copolymer.

The invention further provides a method for treating skin, comprising topically applying to skin in need of treatment for signs of skin aging, acne, or rosacea a composition comprising a retinoid, an HMP, and a cosmetically acceptable topical carrier.

DETAILED DESCRIPTION OF THE INVENTION

Unless defined otherwise, all technical and scientific terms used herein have the same meaning as commonly understood by one of ordinary skill in the art to which the invention belongs. All publications, patent applications, patents, and other references mentioned herein are incorporated by reference.

As used herein, "topically applying" means directly laying on or spreading on outer skin, the scalp, or hair, e.g., by use of the hands or an applicator such as a wipe, roller, or spray.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "cosmetically effective amount" means an amount of a physiologically active compound or composition sufficient for treating one or more signs of skin aging, but low enough to avoid serious side effects. The cosmetically effective amount of the compound or composition will vary with the particular condition being treated, the age and physical condition of the end user, the severity of the condition being treated/prevented, the duration of the treatment, the nature of other treatments, the specific compound or product/composition employed, the particular cosmetically-acceptable carrier utilized, and like factors.

As used herein, "cosmetically acceptable" means that the ingredients the term describes are suitable for use in contact with tissues (e.g., the skin or hair) without undue toxicity, incompatibility, instability, irritation, allergic response, or the like.

As used herein, a "cosmetically acceptable active agent" is a compound (synthetic or natural) that has a cosmetic or therapeutic effect on the skin or hair.

As used herein, "treating" refers to mitigating, reducing, preventing, improving, or eliminating the presence or signs of a condition or disorder.

The present invention is suitable for treating signs of skin aging. As used herein, "signs of skin aging" includes the presence of lines and wrinkles, loss of elasticity, uneven skin, and blotchiness. In a particularly preferred embodiment, the sign of aging is the presence of lines and wrinkles and/or loss of elasticity.

As used herein, "wrinkle" includes fine lines, fine wrinkles, or coarse wrinkles. Examples of wrinkles include, but are not limited to, fine lines around the eyes (e.g., "crow's feet"), forehead and cheek wrinkles, frown-lines, and laugh-lines around the mouth.

As used herein, "loss of elasticity" includes loss of elasticity or structural integrity of the skin or tissue, including but not limited to sagging, lax and loose tissue. The loss of elasticity or tissue structure integrity may be a result of a number of factors, including but not limited to disease, aging, hormonal changes, mechanical trauma, environmental damage, or the result of an application of products, such as a cosmetics or pharmaceuticals, to the tissue.

As used herein, "uneven skin" means a condition of the skin associated with diffuse or mottled pigmentation, which may be classified as hyperpigmentation, such as post-inflammatory hyperpigmentation.

As used herein, "blotchiness" means a condition of the skin associated with redness or erythema.

The invention is also suitable for treating acne. As used herein, "acne" refers to disorders resulting from the actions of hormones and other substances on the sebaceous glands and hair follicles, typically leading to clogged pores and the formation of inflammatory or non-inflammatory lesions on the skin. Specifically, it relates to blemishes, lesions, or pimples, pre-emergent pimples, blackheads, and/or whiteheads. As used herein, a "pre-emergent pimple" is an inflamed follicle that are not visually apparent on the surface of the skin with the naked eye (e.g., as a lesion).

The invention is also suitable for treating rosacea. As used herein, "rosacea" means skin with persistent erythema with or without papules, pustules, or nodules.

Unless otherwise indicated, a percentage or concentration refers to a percentage or concentration by weight (i.e., % (W/W). Unless stated otherwise, all ranges are inclusive of the endpoints, e.g., "from 4 to 9" includes the endpoints 4 and 9.

Where applicable, chemicals are specified according to International Nomenclature of Cosmetic Ingredient (INCI) names. Additional information, including suppliers and trade names, can be found under the appropriate INCI monograph in the *International Cosmetic Ingredient Dictionary and Handbook*, 16$^{th}$ Edition published by the Personal Care Products Council, Washington DC, or via the Personal Care Products Council's On-Line INFOBASE, (available online at online.personalcarecouncil.org).

Low Irritation Polymeric Cleansing Agent (LIPCA)

The composition of the invention comprises one or more low irritation polymeric cleansing agents. For example, the LIPCA may be a superhydrophilic amphiphilic copolymer (SAC) or a low molecular weight hydrophobically modified polymer (HMP).

In one embodiment, the composition comprises at least one SAC.

Suitable SACs are described for example in U.S. Pat. No. 8,258,250, the disclosure of which is incorporated by reference herein.

Synthetic routes for achieving the SACs of the present invention include via post-polymerization modification of precursor polymers comprising superhydrophilic repeat units to render some repeat units amphiphilic. Nonlimiting examples include the reaction of superhydrophilic polymers comprised of repeat units comprising multiple hydroxyl functionalities, for example, starch, hydroxyethylcellulose, dextran, inulin, pullulan, poly(glyceryl methacrylate), poly[tris(hydroxymethyl)acrylamidomethane)], or poly(sucrose methacrylate), with reagents that will result in amphiphilic repeat units. Examples of suitable reaction schemes include:

i) esterification with alkenyl succinic anhydrides,
    ii) etherification with 1,2-epoxyalkanes,
    iii) etherification of with 3-chloro-2-hydroxypropylalkyldimethylammonium chlorides, and
    iv) esterification with monoalkyl phosphate esters.

According to certain preferred embodiments, the SAC for use in the present invention is a polymer having multiple hydroxyl functionalities that is post-polymerization modified to convert some of the repeat units to amphiphilic repeat units. In one particularly preferred embodiment, the polymer, e.g., a starch such as a starch dextrin polymer, is esterified with an alkenyl succinic anhydride to convert some of the superhydrophilic anhydroglucose units to ARUs. The structure of one suitable resulting SAC may be the C-6 sodium dextrin alkenylsuccinate, represented below:

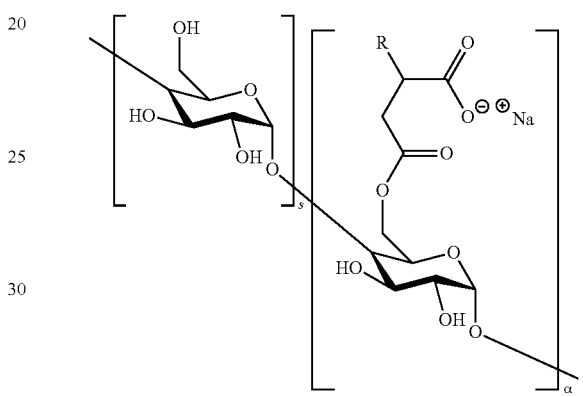

For example, the SAC may be a sodium dextrin dodecenylsuccinate, if $R=C_{12}H_{23}$. As will be recognized by one skilled in the art, such alkenyl succinate esters of polysaccharides may be synthesized as described, for example, in U.S. Pat. No. 2,661,349 incorporated herein by reference. Depending on the nature of the reaction conditions, molecular architecture, type of sugar repeat units, branch points and molecular weight, the modification of the sugar repeat units (anhydroglucose units) may also occur at the C-2, C-3 or C-4 positions in addition to the C-6 position shown above.

The SACs derived from the reaction of the starting polysaccharide with the hydrophobic reagent comprise a polysaccharide bound with the hydrophobic reagent. In certain preferred embodiments, the SAC is a starch-based polysaccharide modified with one or more hydrophobic reagents.

Examples of suitable starches include those derived from such plants as corn, wheat, rice, tapioca, potato, sago, and the like. Such starches can be of a native variety or those developed by plant breeding or by gene manipulation. In an embodiment of the invention, the starches include either the waxy versions of such starches (containing less than 5% amylose), high amylose starches (containing more than 40% amylose), those with a modified chain length (such as those disclosed in U.S. Pat. No. 5,954,883, the disclosure of which is incorporated by reference herein), and/or combinations thereof.

In certain preferred embodiments, the starting starch is potato starch or tapioca starch. In certain other preferred embodiments, the starting starch is a waxy potato starch or waxy tapioca starch. In certain embodiments, the starch-based polysaccharide is modified by dissolving such low molecular weight starch or "dextrin" in water and reacting such starch with a hydrophobic reagent. The starch is desirably processed to lower its molecular weight by techniques known in the art, e.g., action of acid and heat, enzymatic, or thermal processing.

The viscosity of the aqueous solution of the polymeric surfactant is desirably low to minimize the detrimental effect of a high solids level of surfactant with pumping or flow of the solution. For this reason, in an embodiment of the invention, the Brookfield viscosity measured at room temperature (about 23° C.) at 200 rpm using spindle #3 for the polymeric surfactants of this invention may be less than about 1000 cps at 10% aqueous solids based on the total weight of the solution. In another embodiment, the Brookfield viscosity measured at room temperature (about 23° C.) at 200 rpm using spindle #3 of the 10% aqueous solution may be less than about 25 cps. In yet another embodiment, the Brookfield viscosity measured at room temperature (about 23° C.) at 200 rpm using spindle #3 of a 10% aqueous solution will be less than about 10 cps.

In certain preferred embodiments, the starch-based polysaccharide is modified with alkenyl succinic anhydride. Surprisingly, it has been found that a substituted succinic anhydride containing a C12 or longer side chain provides improved foam volume and foam stability than substituted succinic anhydrides having less than a C12 side chain. In certain preferred embodiments, the alkenyl succinic anhydride is dodecenylsuccinic anhydride (DDSA). Exemplary treatment levels of the DDSA, on the dry basis of low molecular weight ranges from about 3 to about 25%. In another embodiment, the treatment level may be from about 5 to about 15% DDSA based on the dry weight of low molecular weight starting starch.

In an embodiment of the invention, the SAC is derived from the reaction of the starting polysaccharide and DDSA, and the bound DDSA on the starch-based polysaccharide may be of from about 3 about 15% based on the weight of dry starch. In another embodiment, the bound DDSA will be between 5 and 12% based on the dry weight of starch.

In an exemplary embodiment of the invention, the hydrophobic reagent is a highly branched version of DDSA containing a 12 carbon side chain made from tetramerization of propene. It has been found that when the tetrapropene is then reacted with maleic anhydride in an ene-type reaction, it forms highly branched tetrapropenyl succinic anhydride (TPSA). Because this material is a slightly viscous oil and has acceptable water solubility (e.g., at about 2-5% in water at 23° C.), this reagent is capable of reacting favorably with the low molecular weight polysaccharide. In an embodiment of this invention, therefore, the hydrophobic reagent used to modify the low molecular weight starch may be TPSA.

In certain other preferred embodiments, the starch-based polysaccharide is modified with a long chain quaternary compound having at least one chain containing 3 or more carbon atoms. In another embodiment the long chain quaternary compound has at least one chain containing 6 or more and more preferably 12 or more carbon atoms, such as 3-chloro-2-hydroxypropyl-dimethyldodecylammonium chloride (sold commercially as QUAB(r) 342 by QUAB Chemicals) or the epoxide form of such compound, 2,3 epoxypropyldimethyldodecylammonium chloride.

In a preferred embodiment of the invention, the SAC is a starch-based polysaccharide derived from potato or tapioca modified with dodecenyl succinic anhydride, wherein the SAC has a mole percent of amphiphilic units that is at least 5 but less than 10% and a weight average molecular weight that is less than about 200,000.

In addition to starch-based polysaccharides, other polysaccharides are suitable for use in the SAC. Such polysaccharides may be derived from plant sources and those based on sugar-type repeat units. Some non-limiting examples of these polysaccharides are guar, xanthan, pectin, carrageenan, locust bean gum, and cellulose, including physical and chemically modified derivatives of the above. In embodiments, physical, chemical and enzymatic degradation of these materials may be necessary to reduce the molecular weight to the desired range to provide the viscosity for the desired application. Chemical modification can also be performed to provide additional functional properties (e.g., cationic, anionic or non-ionic) such as treatment with propylene oxide (PO), ethylene oxide (EO), alkyl chlorides (alkylation) and esterification such as 3-chloro-2-hydroxypropyl-trimethylammonium chloride, sodium tripolyphosphate, chloroacetic acid, epichlorohydrin, phosphorous oxychloride and the like.

In another embodiment, the LIPCA comprises at least one HMP.

Suitable HMPs are described for example in U.S. Pat. No. 8,025,902, the disclosure of which is incorporated by reference herein.

Examples of HMPs include low-molecular weight acrylic, other ethylenically-unsaturated polymers, polyesters, polycarbonates, polyanhydrides, polyamides, polyurethanes, polyureas, polyimides, polysulfones, polysulfides, combinations of two or more thereof, and the like.

Examples of suitable low molecular weight acrylic polymers include hydrophobically-modified acrylic, polysaccharide, cellulose, starch polymers, combinations of two or more thereof, and the like. Suitable low molecular weight acrylic polymers include hydrophobically-modified acrylic polymers, as well as other acrylic polymers, any of which may be formed via solution, suspension, precipitation, dispersion, emulsion, inverse emulsion, microemulsion, micellar polymerization methods, and combinations of two or more thereof. The acrylic polymers for use in the present invention may be derived from any one or more monomers selected from the group consisting of (meth)acrylates, (meth)acrylamides, vinyl ethers, esters, and amides, allyl ethers, esters, amines, and amides, itaconates, crotonates, styrenics, and olefins. The acrylic polymers may be comprised of monomers that are nonionic hydrophilic, nonionic hydrophobic, anionic, cationic, zwitterionic, nonassociative macromeric, associative macromeric, or multifunctional/crosslinking in nature.

As used herein the term "low molecular weight" polymer refers to a polymer having a number average molecular weight ($M_n$) of about 100,000 or less as measured by gel permeation chromatography (GPC) calibrated with a poly (methyl methacrylate) (PMMA) standard. (As used herein, unless otherwise specified, all number average molecular weights ($M_n$) refer to molecular weight measured by gel permeation chromatography (GPC) calibrated with a poly (methyl methacrylate) (PMMA) standard.) In certain preferred embodiments, low-molecular weight polymers are those having molecular weight ranges of from about 5,000 to about 80,000 $M_n$, more preferably from about 10,000 to about 50,000 $M_n$, and more preferably between about 15,000 and 40,000 $M_n$.

Certain HMPs and methods of making such polymers are described in U.S. Pat. No. 6,433,061, issued to Marchant et al., the disclosure of which is incorporated herein by reference. The polymeric materials useful in this invention are preferably non-crosslinked, linear acrylic copolymers that are very mild to the skin and mucosa. These non-crosslinked, linear polymers are preferably of low molecular weight having an $M_n$ of 100,000 or less. The copolymeric compound is polymerized from at least two monomeric components. The first monomeric component is selected from one or more α,β-ethylenically unsaturated monomers containing at least one carboxylic acid group. This acid group can be derived from monoacids or diacids, anhydrides of dicarboxylic acids, monoesters of diacids, and salts thereof. The second monomeric component is hydrophobically modified (relative to the first monomeric component) and is selected from one or more α,β-ethylenically unsaturated non-acid monomers containing a C1 to C9 alkyl group, including linear and branched $C_1$ to $C_9$ alkyl esters of (meth)acrylic acid, vinyl esters of linear and branched $C_1$ to $C_{10}$ carboxylic acids, and mixtures thereof. In one aspect of the invention, the second monomeric component is represented by the formula:

$$CH_2=CRX$$

wherein R is hydrogen or methyl; X is —C(O)OR$_1$ or —OC(O)R$_2$; R$_1$ is linear or branched $C_1$ to $C_9$ alkyl; and R$_2$ is hydrogen or linear or branched $C_1$ to $C_9$ alkyl. In another aspect of the invention R$_1$ and R$_2$ is linear or branched $C_1$ to $C_8$ alkyl and in a further aspect R$_1$ and R$_2$ are linear or branched $C_2$ to $C_5$ alkyl.

Preferably the hydrophobically modified polymers comprise, consist essentially of, or consist of a low molecular weight, non-crosslinked, linear acrylic copolymer derived from at least one first monomeric component selected from the group consisting of (meth)acrylic acid and at least one second monomeric component selected from the group consisting of one or more $C_1$ to $C_9$ alkyl (meth)acrylates, wherein the low molecular weight copolymer has a number average molecular weight of about 100,000 or less.

Exemplary first monomeric components include (meth) acrylic acid, itaconic acid, citraconic acid, maleic acid, fumaric acid, crotonic acid, aconitic acid, and mixtures thereof. Exemplary second monomeric components include ethyl (meth)acrylate, butyl (meth)acrylate, 2-ethylhexyl (meth)acrylate, vinyl formate, vinyl acetate, 1-methylvinyl acetate, vinyl propionate, vinyl butyrate, vinyl 2-ethylhexanoate, vinyl pivalate, vinyl neodecanoate, and mixtures thereof.

As used herein, the terms "(meth)acrylic" acid and "(meth)acrylate" are meant to include the corresponding methyl derivatives of acrylic acid and the corresponding alkyl acrylate. For example, "(meth)acrylic" acid refers to acrylic acid and/or methacrylic acid and "(meth)acrylate" refers to alkyl acrylate and/or alkyl methacrylate.

More preferably, said first monomeric component is selected from the group consisting of (meth)acrylic acid and said second monomeric component is selected from the group consisting of at least one $C_1$ to $C_9$ alkyl (meth) acrylate.

The non-crosslinked, linear acrylic copolymer compounds can be synthesized via free radical polymerization techniques known in the art. In one aspect of the invention, the weight ratio of the first monomeric component to the second monomeric component utilized ranges from about 20:80 to about 50:50. In another aspect the weight ratio of the first monomeric component to the second monomeric component is about 35:65, and in a further aspect the weight ratio of first monomeric component to second monomeric component is about 25:75.

Methods of synthesizing the polymers useful in the compositions and methods of this invention may be found in U.S. Pat. No. 6,433,061 which is hereby incorporated herein by reference.

The linear copolymeric materials useful in the methods and compositions of this invention preferably have a viscosity of 500 mPa·s or less (Brookfield RVT, 20 rpm, spindle no. 1) at a 5 wt. % polymer solids concentration in deionized water and neutralized to pH 7 with an 18 wt. % NaOH solution. The viscosity can range from about 1 to about 500 mPa·s in another aspect, from about 10 to about 250 mPa·s in a further aspect, and from about 15 to about 150 mPa·s in a still further aspect.

In one embodiment, the HMP is a non-crosslinked, linear acrylic copolymer having a number average molecular weight of about 15,000 to about 40,000 and is derived from methacrylic acid and ethylacrylate.

In another embodiment, the HMP is potassium acrylates copolymer.

In one embodiment, the composition comprises about 0.1 to about 10, preferably from about 0.25 to about 5, percent by weight SAC. In another embodiment, the composition comprises about 0.5 to about 2.5 percent by weight SAC. In further embodiment, the composition comprises about 1 to about 2.5 percent by weight SAC.

In one embodiment, the composition comprises about 0.1 to about 5, preferably from about 0.1 to about 2.5, percent by weight HMP. In another embodiment, the composition comprises about 0.5 to about 2.5 percent by weight HMP. In further embodiment, the composition comprises about 1 to about 2.5 percent by weight HMP.

Retinoid

The composition also comprises at least one retinoid. As used herein, "retinoid" means a compound structurally similar to Vitamin A, such as those characterized by this structure:

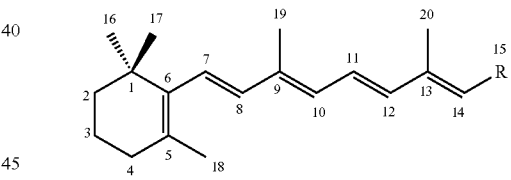

wherein R represents a functional group such as CH$_2$OH (retinol), CHO (retinal), CO$_2$H (retinoic acid), CH$_2$OCOCH (retinyl acetate). Retinoids include other esters such as retinyl palmitate, amine derivatives, and the like. In one embodiment, the retinoid is selected from retinol, retinal, retinoic acid, retinyl acetate, and retinyl palmitate. In a preferred embodiment, the retinoid is retinol.

In one embodiment, the composition comprises about 0.001 to about 5 percent by weight retinoid. In one embodiment, the composition comprises about 0.04 to about 2 percent by weight retinoid. In one embodiment, the composition comprises about 0.04 to about 0.15 percent by weight retinoid.

Topical Composition and Product Forms

The composition may comprise a wide variety of additional oil-soluble materials and/or water-soluble materials conventionally used in compositions for use on skin and hair, at their art-established levels. For example, surfactants, pearlescent or opacifying agents, thickeners, emollients, conditioners, humectants, chelating agents, exfoliants, and additives that enhance the appearance, feel, or fragrance of the cleansing composition, such as colorants, fragrances, preservatives, pH adjusting agents, and the like, can be included.

The composition may comprise one or more other cosmetically acceptable active agents include for example anti-acne agents, shine control agents, anti-microbial agents, anti-inflammatory agents, anti-mycotic agents, anti-parasite agents, external analgesics, sunscreens, photoprotectors, antioxidants, keratolytic agents, surfactants, moisturizers, nutrients, vitamins, energy enhancers, anti-perspiration agents, astringents, deodorants, firming agents, anti-callous agents, agents for hair and/or skin conditioning, and other glycosaminoglycans such as hyaluronic acid.

The amount of cosmetically active agent in may range from about 0.001% to about 20% by weight of the composition, e.g., about 0.005% to about 10% by weight of the composition, such as about 0.01% to about 5% by weight of the composition.

The cosmetically acceptable active agent may be selected for instance from hydroxy acids, benzoyl peroxide, D-panthenol carotenoids, ceramides, polyunsaturated fatty acids, essential fatty acids, enzymes such as laccase, enzyme inhibitors, minerals, hormones such as estrogens, steroids such as hydrocortisone, 2-dimethylaminoethanol, copper salts such as copper chloride, peptides like argireline, syn-ake and those containing copper, coenzyme Q10, amino acids such as proline, vitamins, lactobionic acid, acetyl-coenzyme A, niacin, riboflavin, thiamin, ribose, electron transporters such as NADH and FADH2, natural extracts such as those from aloe vera, feverfew, oatmeal, dill, blackberry, princess tree, picia anomala , and chicory, resorcinols such as 4-hexyl resorcinol, curcuminoids, sugar amines such as N-acetyl glucosamines, and derivatives and mixtures thereof.

Examples of vitamins include, but are not limited to, vitamin A, vitamin B's such as vitamin B3, vitamin B5, and vitamin B12, vitamin C, vitamin K, and different forms of vitamin E like alpha, beta, gamma or delta tocopherols or their mixtures, and derivatives thereof.

Examples of hydroxy acids include, but are not limited to, glycolic acid, lactic acid, malic acid, salicylic acid, citric acid, and tartaric acid.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis.

The composition may further include a cosmetically acceptable topical carrier. The carrier may be from about 50% to about 99.99%, by weight, of the composition (e.g., from about 80% to about 99%, by weight, of the composition). In a preferred embodiment of the invention, the cosmetically acceptable topical carrier includes water.

The composition may be made into a wide variety of product types that include but are not limited to lotions, creams, gels, sticks, sprays, ointments, cleansing liquid washes and solid bars, shampoos and hair conditioners, hair fixers, pastes, foams, powders, mousses, shaving creams, wipes, patches, hydrogels, film-forming products, facial masks and skin masks, films and make-up such as foundations, and mascaras. These product types may contain a variety of cosmetically acceptable topical carriers including, but not limited to solutions, suspensions, emulsions including microemulsions and nanoemulsions, gels, solids and liposomes. The following are non-limiting examples of such carriers. Other carriers can be formulated by those of ordinary skill in the art.

The composition can be formulated as a solution. Solutions typically include an aqueous or organic solvent (e.g., from about 50% to about 99.99% or from about 90% to about 99% of a cosmetically acceptable aqueous or organic solvent). Examples of suitable organic solvents include propylene glycol, polyethylene glycol, polypropylene glycol, glycerol, 1,2,4-butanetriol, sorbitol esters, 1,2,6-hexanetriol, ethanol, and mixtures thereof.

The composition may be formulated as a solution comprising an emollient. Such compositions preferably contain from about 2% to about 50% of an emollient(s). As used herein, "emollients" refer to materials used for the prevention or relief of dryness, such as by preventing the transepidermal loss of water from the skin. Examples of emollients include, but are not limited to, those set forth in the *International Cosmetic Ingredient Dictionary and Handbook*, eds. Pepe, Wenninger and McEwen, pp. 2930-36 (The Cosmetic, Toiletry, and Fragrance Assoc., Washington, D.C., 9th Edition, 2002) (hereinafter "ICI Handbook"). Examples of particularly suitable emollients include vegetable oils, mineral oils, fatty esters, and the like.

A lotion can be made from such a solution. Lotions typically contain from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

The composition alternatively be anhydrous or be an ointment that includes no water but organic and/or silicone solvents, oils, lipids and waxes. An ointment may contain a simple base of animal or vegetable oils or semi-solid hydrocarbons. An ointment may contain from about 2% to about 10% of an emollient(s) plus from about 0.1% to about 2% of a thickening agent(s). Examples of thickening agents include, but are not limited to, those set forth in the ICI Handbook pp. 2979-84.

The composition may be formulated as an emulsion. If the topical carrier is an emulsion, from about 1% to about 10% (e.g., from about 2% to about 5%) of the topical carrier contains an emulsifier(s). Emulsifiers may be nonionic, anionic or cationic. Examples of emulsifiers include, but are not limited to, those set forth in the ICI Handbook, pp.2962-71.

Lotions and creams can be formulated as emulsions. Typically, such lotions contain from 0.5% to about 5% of an emulsifier(s). Such creams typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The composition can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contain between about 0.1% and 5%, by weight, of such gelling agents.

The composition can also be formulated into a solid formulation (e.g., wax-based stick, bar, or powder). It may be loaded onto a substrate, such as a woven or non-woven material, wipe, patch, mask, article of clothing and the like.

In one particular embodiment, the composition comprises at least one polar emollient having a net relative polarity index to the retinoid from about 0.5 to 2, and at least one non-polar emollient having a net relative polarity index to the retinoid from about 7 to about 10, wherein the weight ratio of said polar emollient to said non-polar emollient is from about 95 to 5 to about 40 to 60. For example, the non-polar emollient may be selected from the group consisting of aromatic or linear esters, guerbet ester, mineral oil, squalane, isohexadecane, squalene, liquid paraffin, and mixtures thereof, in particular isohexadecane. The polar emollient may be selected from the group consisting of, propylene glycol stearyl ether, propylene glycol isostearate, and mixtures thereof, in particular propylene glycol stearyl ether.

In another embodiment, the composition comprises an oil-in-water emulsion comprising: (i) about 0.05 to about 0.5% by weight retinol; (ii) propylene glycol stearyl ether; and (iii) isohexadecane, wherein the weight ratio of propylene glycol stearyl ether to isohexadecane is from about 75:25 to about 50:50.

In a further embodiment, the composition is formulated as an emulsion having a water phase and an oil phase, and the LIPCA is contained in the water phase. For example, the composition may be an oil-in-water emulsion in which the water phase contains the LIPCA.

Retinoid Activity

According to the invention, compositions comprising a retinoid along with a LIPCA provide increased retinoid activity, particularly increased retinoid bioactivity.

In one embodiment, the retinoid is retinol and the composition provides at least about a 108%, preferably at least about 125%, increase in retinol bioactivity as measured by a change in cellular retinoic acid binding protein II (CRABPII) gene expression versus the same composition not comprising the low irritation polymeric cleanser.

CRABPII expression is measured by the CRABPII EXPRESSSION TEST conducted in the following manner. One centimeter-diameter ex vivo skin explants are prepared from skin abdominal biopsies. The skin explants are maintained in KGM gold™ culture medium supplemented with amphotericin B, 0.125 µg/ml at 37° C., in a water saturated atmosphere for the 48 hour duration of the test. The explants are placed in a conventional test plate, epidermal surface oriented up, and in sufficient culture medium to nearly but not completely immerse the sample (i.e., the epidermal surface protrudes from the upper surface of the medium). Test composition is applied to the epidermal surface protruding from the culture medium. After 48 hours, using conventional techniques known to those skilled in the art, the explants are removed, from which epidermal mRNA is extracted and expression of CPABPII gene is measured by Quantitative real time PCR (QRT-PCR) using a suitable sequence of oligonucleotides.

The following examples further illustrate the claimed invention.

EXAMPLE 1

The following compositions according to the invention were prepared using the ingredients in Tables 1 and 2.

TABLE 1

| INCI | % wt |
| --- | --- |
| Water | q.s. to 100 wt % |
| Sodium Hydrolyzed Potato Starch Dodecenylsuccinate | 1.20 |
| Sodium Acryloyldimethyltaurate/VP Crosspolymer | 0.50 |
| Disodium EDTA | 0.10 |
| Glycerin | 5.00 |
| Butylene Glycol | 2.00 |
| Sodium Hyaluronate | 0.10 |
| Caprylyl Glycol | 0.50 |
| Stearyl Alcohol (and) Ceteareth-20 | 3.00 |
| Cetearyl Alcohol (and) Ceteareth-20 | 3.00 |
| Isohexadecane | 1.50 |
| PPG-15 Stearyl Ether | 4.50 |
| Pentaerythrityl Tetraethylhexanoate | 7.00 |
| BHT | 0.10 |
| Polyacrylamide (and) Laureth-7 (and) C13-14 Isoparaffin | 1.00 |
| Dimethicone (and) Dimethicone Crosspolymer | 5.00 |
| Dimethicone (and) Trisiloxane | 3.00 |
| Ascorbic Acid | 0.05 |
| Polysorbate 20 (and) Retinol | 0.23 |
| Phenoxyethanol | 0.50 |
| Chlorphenesin | 0.20 |
| Sodium Hydroxide | q.s. to pH 6.5-6.8 |
| Fragrance | 0.30 |
| Polyethylene (and) PTFE | 0.50 |
| Water (and) Hydrolyzed Myrtus Communis Leaf Extract | 4.00 |

Composition 1 was prepared as follows:
Premix 1: Mixed Ascorbic Acid with 2% of total batch water and adjusted pH to ~5. Post added under 40° C.
Main Phase: Introduced Sodium Hydrolyzed Potato Starch Dodecenylsuccinate into the main mixing vessel and slowly added Water and mixed until homogeneous. Next Sodium Acryloyldimethyltaurate/VP Crosspolymer was added and mixed until uniform. Then Disodium EDTA was added and mixed in until the batch was homogeneous and solid polymers were fully hydrated before proceeding. Added Glycerin and Butylene Glycol to the batch and mixed until homogeneous.
Began heating the batch to target 73° C. Once batch reached 65° C., added Caprylyl Glycol, Chlorphenesin, Phenoxyethanol, and Sodium Hyaluronate.
Oil Phase: In a separate container added the following ingredients and heated to target 73° C. while mixing.
Isohexadecane
PPG 15 Stearyl Ether
Pentaerythrityl Tetraethylhexanoate
Dimethicone (and) Dimethicone Crosspolymer
Dimethicone (and) Trisiloxane (and) Dimethicone (and) Dimethicone
Stearyl Alcohol (and) Ceteareth-20

Cetearyl Alcohol (and) Ceteareth-20

Next added BHT to the oil phase 5 minutes before emulsification.

Emulsification: When the main phase and oil phase were at 73° C., slowly added the oil phase to the water phase. Mixed 10-15 min and added Polyacrylamide (and) Laureth-7 (and) C13-14 Isoparaffin. Next homogenized the batch for 1 min and began to cool the batch to below 40° C.

Post Adds: Once the batch was at or below 40° C., added Polyethylene (and) PTFE, Premix 1 (Ascorbic Acid), Water (and) Hydrolyzed Myrtus Communis Leaf Extract, and Fragrance. Next measured the pH of the batch, and adjusted to target pH of 6.5-6.8 using 20% Sodium Hydroxide solution.

Under Yellow Light and Argon Gas atmosphere, added Retinol and mixed thoroughly for 10-15 min. Batch was done when the batch temperature was cooled to 30-35° C.

TABLE 2

| INCI | % wt |
| --- | --- |
| Water | q.s. to 100 wt % |
| Potassium Acrylates Copolymer | 4.00 |
| Sodium Acryloyldimethyltaurate/VP Crosspolymer | 0.50 |
| Disodium EDTA | 0.10 |
| Glycerin | 5.00 |
| Butylene Glycol | 2.00 |
| Sodium Hyaluronate | 0.10 |
| Caprylyl Glycol | 0.50 |
| Stearyl Alcohol (and) Ceteareth-20 | 3.00 |
| Cetearyl Alcohol (and) Ceteareth-20 | 3.00 |
| Isohexadecane | 1.50 |
| PPG-15 Stearyl Ether | 4.50 |
| Pentaerythrityl Tetraethyl hexanoate | 7.00 |
| BHT | 0.10 |
| Polyacrylamide (and) Laureth-7 (and) C13-14 Isoparaffin | 1.00 |
| Dimethicone (and) Dimethicone Crosspolymer | 5.00 |
| Dimethicone (and) Trisiloxane | 3.00 |
| Ascorbic Acid | 0.05 |
| Polysorbate 20 (and) Retinol | 0.23 |
| Phenoxyethanol | 0.50 |
| Chlorphenesin | 0.20 |
| Sodium Hydroxide | q.s. to pH 6.5-6.8 |
| Fragrance | 0.30 |
| Polyethylene (and) PTFE | 0.50 |
| Water (and) Hydrolyzed Myrtus Communis Leaf Extract | 4.00 |

Composition 2 was prepared as follows:

Premix 1: Mixed Ascorbic Acid with 2% of water and adjusted to pH ~5. Post added under 40° C.

Main Phase: Introduced water into the main mixing vessel and added Sodium Acryloyldimethyltaurate/VP Crosspolymer under high mixing and mixed until uniform. Then added Disodium EDTA and mixed until the batch was homogeneous and fully hydrated before proceeding. Added Glycerin and Butylene Glycol to the batch and mixed until homogeneous.

Began heating the batch to target 73° C. At above 65° C. added Caprylyl Glycol, Chlorphenesin, Phenoxyethanol, and Sodium Hyaluronate. Then added Potassium Acrylates Copolymer and adjusted pH with 10% Sodium Hydroxide solution to 6.0-6.5 or until the batch became clear.

Oil Phase: In a separate container added the following and heated to target 73° C. while mixing.

Isohexadecane

PPG 15 Stearyl Ether

Pentaerythrityl Tetraethylhexanoate

Dimethicone; Dimethicone Crosspolymer

Dimethicone; Trisiloxane;

Stearyl Alcohol; Ceteareth-20

Cetearyl Alcohol; Ceteareth-20

Next added BHT to the oil phase 5 minutes before emulsification.

Emulsification: When the main phase and oil phase were at 73° C., slowly added the oil phase to the water phase. Mixed 10-15 min and added Polyacrylamide; Laureth-7; C13-14 Isoparaffin. Next homogenized the batch for 1 min and began to cool the batch to below 40° C.

Post Adds: Once the batch was at or below 40° C., added Polyethylene; PTFE, Premix 1 (Ascorbic Acid), Hydrolyzed Myrtus Communis Leaf Extract, and Fragrance. Next measured the pH of the batch, and adjusted to target of 6.5-6.8.

Under Yellow Light and Argon Gas, added Retinol and mixed thoroughly for 10-15 min. Batch was done when the batch temperature is 30-35° C.

EXAMPLE 2

The two compositions of Example 1 were compared with NEUTROGENA® Rapid Wrinkle Repair® commercially available from Johnson & Johnson Consumer Inc., which contains 0.1% retinol but no LIPCA, for in vitro retinol bioactivity. Retinol activity was measured by assessing the expression of two gene markers relevant for retinoid activity in the epidermis, the Heparin Binding Epidermal Growth Factor ("HB-EGF") and the Cellular Retinoic Acid Binding Protein2 ("CRABPII"). The tests were performed as follows.

One centimeter-diameter ex vivo skin explants were prepared from skin abdominal biopsies. The skin explants were maintained in KGM gold™ culture medium supplemented with amphotericin B, 0.125 µg/ml at 37° C., in a water saturated atmosphere for the 48 hour duration of the test. The explants were placed in a conventional test plate, epidermal surface oriented up, and in sufficient culture medium to nearly but not completely immerse the sample (i.e., the epidermal surface protruded from the upper surface of the medium). Test formulations were applied to the skin explants for 24 hours and gene expression was measured in the epidermis by quantitative PCR. After 48 hours, using conventional techniques known to those skilled in the art, the explants are removed, from which epidermal mRNA was extracted and expression of CPABPII and HB-EGF genes were measured by Quantitative real time PCR (QRT-PCR) using a suitable sequence of oligonucleotides.

The results are shown in Tables 3 and 4 as fold-changes from untreated control.

TABLE 3

| Treatment | Percent Change from Normalized Untreated (CRABPII gene expression) | Std. deviation |
| --- | --- | --- |
| Untreated | 100 | 7.26 |
| NEUTROGENA ® Rapid Wrinkle Repair ® (Comparative) | 640 | 100.13 |
| Composition 2 | 793 | 60.51 |
| Composition 1 | 693 | 129.50 |

TABLE 4

| Treatment | Percent Change from Normalized Untreated (HB-EGF gene expression) | Std. deviation |
|---|---|---|
| Untreated | 100 | 18.02 |
| NEUTROGENA ® Rapid Wrinkle Reducer ® (Comparative) | 1104 | 309.36 |
| Composition 2 | 1472 | 216.14 |
| Composition 1 | 1211 | 258.09 |

The retinol activity was greater in the formulations according to the invention containing retinol in combination with a LIPCA than retinol alone. In particular, the Table 2 composition containing potassium acrylates copolymer and retinol had the highest retinol activity.

These results demonstrate that addition of a LIPCA into a retinol formulation increases the activity of the retinol by increasing the expression of genes associated with anti-aging benefits.

The invention claimed is:

1. A topical composition comprising a retinoid selected from the group consisting of retinol, retinal, retinoic acid, retinyl acetate, and retinyl palmitate, sodium dextrin dodecenylsuccinate and a cosmetically acceptable topical carrier.

2. A composition comprising about 0.001 to about 5 weight percent retinol and about 0.1 to about 5 weight percent sodium potato dextrin dodecenylsuccinate, wherein said composition is an oil-in-water emulsion.

* * * * *